United States Patent
Jenkins et al.

(10) Patent No.: US 6,815,555 B2
(45) Date of Patent: Nov. 9, 2004

(54) SUBSTITUTED PHENOL COMPOUNDS USEFUL FOR ANESTHESIA AND SEDATION

(75) Inventors: Thomas E. Jenkins, La Honda, CA (US); Yu-Hua Ji, Redwood City, CA (US); Huiwei Wu, Foster City, CA (US); Jennifer Bolton, San Francisco, CA (US)

(73) Assignee: Theravance, Inc., South San Franciso, CA (US)

( * ) Notice: Subject to any disclaimer, the term of this patent is extended or adjusted under 35 U.S.C. 154(b) by 118 days.

(21) Appl. No.: 10/255,889

(22) Filed: Sep. 26, 2002

(65) Prior Publication Data

US 2003/0119790 A1 Jun. 26, 2003

Related U.S. Application Data

(60) Provisional application No. 60/325,044, filed on Sep. 26, 2001.

(51) Int. Cl.$^7$ ............................................. C07C 69/76
(52) U.S. Cl. ........................ 560/7.5; 560/67; 558/257; 562/888; 514/532
(58) Field of Search ........................ 558/257; 514/532; 560/67; 562/888

(56) References Cited

U.S. PATENT DOCUMENTS

| | | |
|---|---|---|
| 3,029,276 A | 4/1962 | Hausweiler et al. |
| 3,112,338 A | 11/1963 | Smutny et al. |
| 3,642,868 A | 2/1972 | Dexter et al. |
| 3,790,648 A | 2/1974 | Schmidt et al. |
| 3,808,296 A | 4/1974 | Brunetti et al. |
| 3,887,638 A | 6/1975 | Crescentini et al. |
| 4,228,235 A | 10/1980 | Okonogi et al. |
| 5,155,122 A | 10/1992 | Connor et al. |
| 5,395,752 A | 3/1995 | Law et al. |
| 5,510,361 A | 4/1996 | Scherz et al. |
| 5,879,894 A | 3/1999 | Law et al. |
| 5,908,869 A | 6/1999 | Jones et al. |
| 6,204,257 B1 | 3/2001 | Stella et al. |

FOREIGN PATENT DOCUMENTS

| | | |
|---|---|---|
| EP | 636647 A1 | 2/1995 |
| GB | 1324055 | 7/1973 |
| JP | 59072443 | 4/1984 |
| JP | 61020856 | 1/1986 |
| JP | 61-218558 | 9/1986 |
| WO | WO 99/58555 | 11/1999 |
| WO | WO 00/07972 | 2/2000 |
| WO | WO 00/48572 | 8/2000 |
| WO | WO 01/26656 A2 | 4/2001 |

OTHER PUBLICATIONS

Trapani et al., "Propofol Analogues, Synthesis, Relationships between Structure and Affinity at GABA$_A$ Receptor in Rat Brain, and Differential Electrophysiological Profile at Recombinant Human GABA$_A$ Receptors", J. Med. Chem., vol. 41, pp 1846–1854 (1998).

Cooke et al., "Water–Soluble Propofol Analogues with Intravenous Anaesthetic Activity", Bioorganic & Medicial Chemistry Letters, 11:927–930 (2001).

James et al., "Synthesis, Biological Evaluation, and Preliminary Structure–Activity Considerations of a Series of Alkylphenols as Intravenous Anesthetic Agents", J. Med. Chem., 23:1350–1357 (1980).

Krasowski et al., "General Anesthetic Potencies of a Series of Propofol Analogs Correlate with Potency for Potentiation of Y–Aminobutyric Acid (GABA) Current at the GABA$_A$ Receptor but Not with Lipid Solubility", J. of Pharmacology and Experimental Therapeutics, 297:338–351 (2001).

*Primary Examiner*—Paul J. Killos
(74) *Attorney, Agent, or Firm*—Roberta P. Saxon; Joyce G. Cohen; Jeffrey A. Hagenah

(57) ABSTRACT

The invention provides substituted phenol compounds and pharmaceutical compositions containing substituted phenol compounds which are useful for inducing or maintaining anesthesia or sedation in a mammal. This invention also provides methods for inducing or maintaining anesthesia or sedation in a mammal using substituted phenol compounds.

23 Claims, No Drawings

SUBSTITUTED PHENOL COMPOUNDS USEFUL FOR ANESTHESIA AND SEDATION

CROSS-REFERENCE TO RELATED APPLICATIONS

This application claims the benefit of U.S. Provisional Application No. 60/325,044, filed on Sep. 26, 2001; the entire disclosure of which is incorporated herein by reference in its entirety.

FIELD OF THE INVENTION

This invention is directed to substituted phenol compounds; pharmaceutical compositions containing substituted phenol compounds; and methods of using such compounds and compositions to induce or maintain general anesthesia or sedation in a mammal. This invention is also directed to processes and intermediates useful for preparing substituted phenol compounds.

BACKGROUND OF THE INVENTION

Propofol (i.e., 2,6-diisopropylphenol) is an injectable anesthetic used to induce and maintain general anesthesia and sedation. Because of its beneficial properties and ease of administration, propofol is widely-used for both human and veterinary applications.

One drawback of propofol is that it is retained in the body and metabolized relatively slowly. Therefore, patient recovery can be unpredictable and is often dependent on the total amount of propofol administered.

Accordingly, a need exists for novel anesthetic agents. In particular, a need exists for novel anesthetic agents having a predictable duration of action.

SUMMARY OF THE INVENTION

The present invention provides substituted phenol compounds and pharmaceutical compositions containing substituted phenol compounds, which compounds and compositions are useful for inducing and maintaining general anesthesia or sedation in a mammal. The substituted phenol compounds of this invention contain a reactive functional group which allows the compounds to be converted (i.e., hydrolyzed or metabolized) in vivo into an inactive derivative. Thus, the substituted phenol compounds of this invention have a predictable duration of action when administered to a patient.

Accordingly, in one of its composition aspects, this invention provides a pharmaceutical composition comprising a pharmaceutically acceptable carrier and a compound selected from the group consisting of:

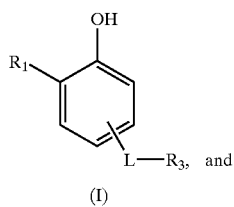

formula (I)

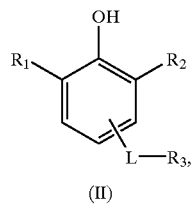

formula (II)

wherein
$R_1$ and $R_2$ are each independently $(C_1-C_8)$alkyl, $(C_3-C_8)$cycloalkyl, or $(C_3-C_8)$cycloalkyl$(C_1-C_8)$alkyl;
L is selected from the group consisting of covalent bond and a hydrocarbylene group containing from 1 to about 12 carbon atoms and optionally containing from 1 to about 5 heteroatoms selected from the group consisting of oxygen, nitrogen, and sulfur; and
$R_3$ is selected from the group consisting of —C(=O)$OR_a$, —C(=O)$SR_a$, —P(=O)$(OR_a)_2$, —C(=O)OCH$_2$C(=O)N$(R_a)_2$, and —C(=O)OC(=O)$R_a$ wherein each $R_a$ is independently selected from a hydrocarbyl group containing from 1 to about 20 carbon atoms and optionally containing from 1 to about 5 heteroatoms selected from the group consisting of halo, nitrogen, oxygen and sulfur;
or a pharmaceutically acceptable salt thereof.

In another of its composition aspects, this invention provides a compound of formula (V):

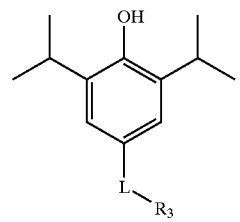

(V)

wherein L is a covalent bond, methylene, or ethylene; and $R_3$ is as defined herein;
provided when L is a covalent bond, $R_3$ is not —C(=O)$OR_a$ wherein $R_a$ is methyl, ethyl, 1,2-dibromoethyl, but-2-enyl, hexadecyl, stearyl, or benzyl; and
provided when L is ethylene, $R_3$ is not —C(=O)$OR_a$ wherein $R_a$ is methyl or stearyl;
or a pharmaceutically acceptable salt thereof.

In yet another of its composition aspects, this invention provides a compound of formula (X):

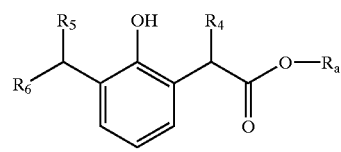

(X)

wherein
$R_4$ is $(C_1-C_5)$alkyl, $(C_2-C_5)$alkenyl, or $(C_2-C_5)$alkynyl;
$R_5$ is $(C_1-C_6)$alkyl, $(C_3-C_8)$cycloalkyl, or $(C_3-C_8)$cycloalkyl$(C_1-C_6)$alkyl; and
$R_6$ is methyl;
or $R_5$ and $R_6$ together with the carbon atom to which they are attached form a $(C_{3-8})$cycloalkyl; and $R_a$ is $(C_1-C_8)$alkyl, $(C_2-C_8)$alkenyl, $(C_2-C_8)$ alkynyl, or $(C_3-C_8)$cycloalkyl.

The substituted phenol compounds and pharmaceutical compositions of this invention are useful for inducing or maintaining anesthesia or sedation in a mammal, such as a human or domesticated mammal.

Accordingly, in one of its method aspects, this invention is directed to a method for inducing or maintaining anesthesia or sedation in a mammal, comprising administering to a mammal an anesthesia or sedation-producing amount of a pharmaceutical composition comprising a pharmaceutically acceptable carrier and a compound selected from formulae (I) or (II), or a pharmaceutically acceptable salt thereof.

The invention also provides substituted phenol compounds for use in medical therapy (e.g. for inducing or maintaining anesthesia or sedation). Additionally, this invention provides substituted phenol compounds for use in the manufacture of a medicament useful for inducing or maintaining anesthesia or sedation in a mammal (e.g. a human).

The invention also provides processes and intermediates disclosed herein that are useful for preparing substituted phenol compounds, or that are useful for preparing compositions comprising substituted phenol compounds.

DETAILED DESCRIPTION

When describing the compounds, compositions and methods of this invention, the following terms have the following meaning unless otherwise indicated: halo is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic.

The term "hypnotic agent" refers generally to a compound that promotes sleep or is used to induce or maintain anesthesia or sedation.

The term "anesthesia" as used herein refers to a loss of sensation resulting from pharmacologic depression of nerve function.

The term "sedation" is defined herein as the calming of mental excitement or abatement of physiological function by administration of a drug.

The term "effective amount" refers to that amount which is sufficient to induce or maintain anesthesia or sedation when administered to a mammal; i.e., an anesthesia- or sedation-producing amount. This amount will vary depending on the subject and the manner of administration, and can be determined routinely by one of ordinary skill in the art.

The term "analgesic" refers to a compound that relieves pain by altering perception of nociceptive stimuli without producing significant anesthesia or loss of consciousness.

The term "opioid" refers to synthetic narcotics that have opiate-like activities (e.g., induction of sleep).

The term "linking group," identified by the symbol L, refers to a hydrocarbylene group which links the phenol ring to the reactive functional group in the substituted phenol compounds of this invention. Preferably, the linking group is a covalent bond or a hydrocarbylene group containing from about 1 to about 12 carbon atoms and optionally containing from 1 to about 5 heteroatoms selected from the group consisting of oxygen, nitrogen and sulfur. Typically, a linking group separates the reactive functional group (e.g. $R_3$) from the phenol ring by about 5 to about 100 angstroms, or preferably by about 5 to about 20 angstroms. Suitable linking groups include divalent alkylene, alkenylene, and alkynylene chains. In addition, the linker can incorporate ether or thioether groups within the chain; the linking group can also be linked to the reactive functional group or to the phenol ring through ether or thioether groups.

The term "reactive functional group," identified by the symbol $R_3$, refers to a functional group which is converted (e.g. hydrolyzed or metablized) in vivo to a functional group which renders the resulting compound essentially inactive as an anesthetic or sedative agent in vivo. The term reactive functional group includes, by way of illustration, carboxylic acid esters and thioesters; phosphonic acid esters and thioesters; carboxylic acid anhydrides and the like; which are converted in vivo to provide the corresponding carboxylic or phosphonic acid.

The term reactive functional group also includes other hydrophobic groups that are degraded enzymatically in vivo to provide a group that deactivates the substituted phenol compound (e.g. by preventing the resulting derivative from crossing the blood-brain barrier) and/or that provide a derivative that is essentially inactive in vivo.

The reactive functional group can be linked directly to any carbon atom of the phenol ring by a covalent bond. Alternatively, the reactive functional group can be linked to the phenol ring through a linker, which can be attached to any carbon atom of the phenol ring by a covalent bond.

The term "hydrocarbyl" refers to a monovalent organic radical composed primarily of carbon and hydrogen and which may optionally contain 1 to about 5 heteroatoms selected from the group consisting of halo, nitrogen, oxygen and sulfur. Such hydrocarbyl groups may be aliphatic, alicyclic, aromatic or combinations thereof (e.g. aralkyl or alkaryl) and include, by way of illustration, groups such as alkyl, alkenyl, alkynyl, cycloalkyl, cycloalkenyl, aryl, aralkyl and alkaryl groups.

The term "hydrocarbylene" refers to a divalent organic radical composed primarily of carbon and hydrogen and which may optionally contain 1 to about 5 heteroatoms selected from the group consisting of halo, nitrogen, oxygen and sulfur. Such hydrocarbylene groups may be aliphatic, alicyclic, aromatic or combinations thereof (e.g. aralkylene or alkarylene) and include, by way of illustration, groups such as alkylene, alkenylene, alkynylene, arylene, aralkylene and alkarylene groups.

The term "carboxylic acid ester" refers to a group of the formula —C(O)OR, where R is a hydrocarbyl group containing from about 1 to about 12 carbon atoms and optionally containing 1 to about 5 heteroatoms selected from the group consisting of halo, nitrogen, oxygen and sulfur. Representative carboxylic acid ester groups include, for example, methoxycarbonyl, ethoxycarbonyl, isopropoxycarbonyl, phenoxycarbonyl, benzyloxycarbonyl, and the like.

The term "carboxylic acid thioester" refers to a group of the formula —C(O)SR, where R is a hydrocarbyl group containing from about 1 to about 12 carbon atoms and optionally containing 1 to about 5 heteroatoms selected from the group consisting of halo, nitrogen, oxygen and sulfur. Representative carboxylic acid thioester groups include, for example, thiomethoxycarbonyl, thioethoxycarbonyl, and the like.

The term "phosphonic acid ester" refers to a group of the formula —P(O)(OR)$_2$, where each R is independently a hydrocarbyl group containing from about 1 to about 12 carbon atoms and optionally containing 1 to about 5 heteroatoms selected from the group consisting of halo, nitrogen, oxygen and sulfur. Representative phosphonic acid ester groups include, for example, dimethoxyphosphono, diethoxyphosphono, diphenoxyphosphono, dibenzyloxyphosphono, and the like.

The term "phosphonic acid thioester" refers to a group of the formula —P(O)(SR)$_2$, where each R is independently a hydrocarbyl group containing from about 1 to about 12 carbon atoms and optionally containing 1 to about 5 heteroatoms selected from the group consisting of halo, nitrogen, oxygen and sulfur. Representative phosphonic acid thioester groups include, for example, dithiomethoxyphosphono, dithioethoxyphosphono, and the like.

The term "carboxylic acid anhydride" refers to a group of the formula —C(O)OC(O)R, where R is a hydrocarbyl group containing from about 1 to about 12 carbon atoms and optionally containing 1 to about 5 heteroatoms selected from the group consisting of halo, nitrogen, oxygen and sulfur. Representative carboxylic acid anhydride groups include, for example, (tert-butylcarbonyloxy)carbonyl, and the like.

It will be appreciated by those skilled in the art that compounds having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

For any group described herein that can be optionally substituted, it is understood that such groups do not contain any substitution or substitution patterns which are sterically impractical and/or synthetically non-feasible.

While a broad definition of the invention is set forth in the Summary of the Invention, certain compounds or compositions may be preferred. Specific and preferred values listed herein for radicals, substituents, and ranges, are for illustration only; they do not exclude other defined values or other values within defined ranges for the radicals and substituents.

In one embodiment, a compound that can be incorporated into the pharmaceutical compositions of the invention and that can be administered according to the methods of the invention is a compound of Formula (I):

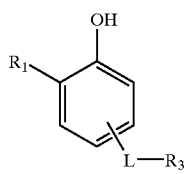

(I)

wherein L and R$_3$ are as defined herein; and R$_1$ is (C$_1$–C$_8$) alkyl, (C$_3$–C$_8$)cycloalkyl, or (C$_3$–C$_8$)cycloalkyl(C$_1$–C$_8$) alkyl.

In another embodiment, a compound that can be incorporated into the pharmaceutical compositions of the invention and that can be administered according to the methods of the invention is a compound of formula (II):

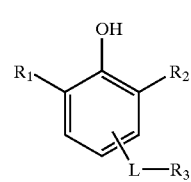

(II)

wherein L and R$_3$ are as defined herein; and R$_1$ and R$_2$ are each independently (C$_1$–C$_8$)alkyl, (C$_3$–C$_8$)cycloalkyl, or (C$_3$–C$_8$)cycloalkyl(C$_1$–C$_8$)alkyl.

In another embodiment, a compound that can be incorporated into the pharmaceutical compositions of the invention and that can be administered according to the methods of the invention is a compound of formula (III):

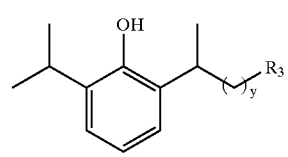

(III)

wherein y is 0, 1, 2, 3, 4, 5, or 6; and R$_3$ is as defined herein.

Another compound that can be incorporated into the pharmaceutical compositions of the invention and that can be administered according to the methods of the invention is a compound of formula (IV):

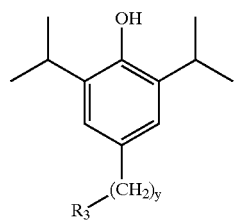

(IV)

wherein y is 0, 1, 2, 3, 4, 5, or 6; and R$_3$ is as defined herein.

Specifically, (C$_1$–C$_8$)alkyl can be methyl, ethyl, propyl, isopropyl, butyl, iso-butyl, sec-butyl, pentyl, 2-pentyl, 3-pentyl, hexyl, 2-hexyl, heptyl, 2-heptyl, octyl, or 2-octyl; (C$_3$–C$_8$)cycloalkyl can be cyclopropyl, cyclobutyl, cyclopentyl, cyclohexyl, cycloheptyl, or cyclooctyl; (C$_3$–C$_8$)cycloalkyl(C$_1$–C$_8$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; (C$_1$–C$_8$)alkoxy can be methoxy, ethoxy, propoxy, isopropoxy, butoxy, iso-butoxy, sec-butoxy, pentoxy, 3-pentoxy, hexyloxy, heptyloxy, or oxyloxy; (C$_2$-C$_8$)alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, 2,4-hexadienyl, or 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl; (C$_2$–C$_8$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 2,4-hexadienyl, 5-hexynyl, 1-heptynyl, 2-heptynyl, 3-heptynyl, 4-heptynyl, 5-heptynyl, 6-heptynyl, 1-octynyl, 2-octynyl, 3-octynyl, 4-octynyl, 5-octynyl, 6-octynyl, or 7-octynyl; (C$_1$–C$_8$)alkanoyl can be acetyl, propanoyl, butanoyl, pentanoyl, hexanoyl, heptanoyl, or octanoyl; (C$_1$–C$_8$)

alkoxycarbonyl can be methoxycarbonyl, ethoxycarbonyl, propoxycarbonyl, isopropoxycarbonyl, butoxycarbonyl, pentoxycarbonyl, hexyloxycarbonyl, heptyloxycarbonyl, or octyloxycerbonyl; $(C_1–C_8)$alkylene can be methylene, ethylene, propylene, isopropylene, butylene, iso-butylene, sec-butylene, pentylene, 2-pentylene, 3-pentylene, hexylene, 2-hexylene, heptylene, 2-heptylene, octylene, or 2-octylene; $(C_3–C_8)$cycloalkylene can be cyclopropylene, cyclobutylene, cyclopentylene, cyclohexylene, cycloheptylene, or cyclooctylene; $(C_2–C_8)$alkenylene can be vinylene, allylene, 1-propenylene, 2-propenylene, 1-butenylene, 2-butenylene, 3-butenylene, 1-pentenylene, 2-pentenylene, 3-pentenylene, 4-pentenylene, 1-hexenylene, 2-hexenylene, 3-hexenylene, 4-hexenylene, 2,4-hexadienylene, or 5-hexenylene, 1-heptenylene, 2-heptenylene, 3-heptenylene, 4-heptenylene, 5-heptenylene, 6-heptenylene, 1-octenylene, 2-octenylene, 3-octenylene, 4-octenylene, 5-octenylene, 6-octenylene, 7-octenylene; $(C_2–C_8)$alkynylene can be ethynylene, 1-propynylene, 2-propynylene, 1-butynylene, 2-butynylene, 3-butynylene, 1-pentynylene, 2-pentynylene, 3-pentynylene, 4-pentynylene, 1-hexynylene, 2-hexynylene, 3-hexynylene, 4-hexynylene, 2,4-hexadiynylene, 5-hexynylene, 1-heptynylene, 2-heptynylene, 3-heptynylene, 4-heptynylene, 5-heptynylene, 6-heptynylene, 1-octynylene, 2-octynylene, 3-octynylene, 4-octynylene, 5-octynylene, 6-octynylene, or 7-octynylene; and aryl can be phenyl, indenyl, or naphthyl.

Specifically, $R_1$ and $R_2$ are each independently selected from the group consisting of $(C_1–C_8)$alkyl and $(C_3–C_8)$cycloalkyl.

Specifically, $R_1$ and $R_2$ are each independently selected from the group consisting of $(C_1–C_6)$alkyl and $(C_3–C_6)$cycloalkyl.

Preferably, $R_1$ and $R_2$ are each independently isopropyl, 2-butyl, 2-pentyl, 3-pentyl, 2-hexyl, 3-hexyl, or $(C_3–C_6)$cycloalkyl.

Specifically, $R_1$ and $R_2$ are each independently selected from the group consisting of $(C_2–C_4)$alkyl and $(C_3–C_6)$cycloalkyl.

Specifically, $R_1$ and $R_2$ are each independently $(C_1–C_6)$alkyl.

More specifically, $R_1$ and $R_2$ are each independently selected from the group consisting of $(C_2–C_4)$alkyl.

More preferably, $R_1$ and $R_2$ are each isopropyl.

Specifically, $R_3$ is —C(=O)OR$_a$, —C(=O)SR$_a$, —P(=O)(OR$_a$)$_2$, —C(=O)OCH$_2$C(=O)N(R$_a$)$_2$, or —C(=O)OC(=O)R$_a$ wherein R$_a$ is $(C_1–C_8)$alkyl, $(C_2–C_8)$alkenyl, $(C_2–C_8)$ alkynyl, $(C_3–C_8)$cycloalkyl, $(C_3–C_8)$cycloalkenyl, $(C_3–C_8)$ cycloalkyl$(C_1–C_8)$alkyl, $(C_3–C_8)$cycloalkenyl$(C_1–C_8)$alkyl, aryl, aryl$(C_1–C_8)$alkyl,aryl$(C_1–C_8)$ alkenyl, or aryl$(C_1–C_8)$alkynyl wherein any $(C_1–C_8)$alkyl, $(C_1–C_8)$alkenyl, $(C_1–C_8)$alkynyl, $(C_3–C_8)$cycloalkyl, or aryl is optionally substituted by one or more halo, cyano, $(C_1–C_8)$alkoxycarbonyl, $(C_1–C_8)$alkanoyl, or $(C_1–C_8)$alkoxy.

Specifically, $R_3$ is —C(=O)OR$_a$, —C(=O)SR$_a$, or —C(=O)OC(=O)R$_a$ wherein R$_a$ is $(C_1–C_8)$alkyl, $(C_2–C_8)$alkenyl, $(C_2–C_8)$alkynyl, $(C_3–C_8)$cycloalkyl, $(C_3–C_8)$cycloalkenyl, $(C_3–C_8)$cycloalkyl$(C_1–C_8)$alkyl, $(C_3–C_8)$cycloalkenyl $(C_1–C_8)$alkyl,aryl,aryl$(C_1–c_8)$alkyl, aryl $(C_1–C_8)$alkenyl, or aryl$(C_1–C_8)$alkynyl wherein any $(C_1–C_8)$alkyl, $(C_1–C_8)$alkenyl, $(C_1–C_8)$alkynyl, $(C_3–C_8)$cycloalkyl, or aryl is optionally substituted by one or more halo, cyano, $(C_1–C_8)$alkoxycarbonyl, $(C_1–C_8)$alkanoyl, or $(C_1–C_8)$alkoxy.

More specifically, $R_3$ is —C(=O)OR$_a$, —C(=O)SR$_a$, or —C(=O)OC(=O)R$_a$.

More specifically, $R_3$ is —C(=O)OR$_a$.

Specifically, R$_a$ is $(C_1–C_8)$alkyl, $(C_2–C_8)$alkenyl, $(C_2–C_8)$ alkynyl, $(C_3–C_8)$cycloalkyl, aryl, aryl$(C_1–C_8)$alkyl, aryl $(C_1–C_8)$alkenyl, or aryl $(C_1–C_8)$alkynyl.

More specifically, R$_a$ is $(C_1–C_8)$alkyl, $(C_2–C_8)$alkenyl, $(C_2–C_8)$alkynyl, or $(C_3–C_8)$cycloalkyl.

More specifically, R$_a$ is $(C_1–C_6)$alkyl, $(C_2–C_6)$alkenyl, or $(C_2–C_6)$alkynyl.

More specifically, R$_a$ is methyl, ethyl, propyl, isopropyl, 2-butyl, or benzyl.

Preferably, L is selected from the group consisting of a covalent bond and a hydrocarbylene group containing from about 1 to about 8 carbon atoms and optionally containing from 1 to about 5 heteroatoms selected from the group consisting of oxygen, nitrogen and sulfur.

Specifically, L is a bond, $(C_1–C_6)$alkylene, $(C_2–C_6)$ alkenylene, or $(C_2–C_6)$alkynylene.

More specifically, L is methylene, ethylene, vinylene, propylene, allylene, butylene, pentylene, or hexylene.

A preferred value for L is a covalent bond, methylene, ethylene, or vinylene.

In one embodiment, a preferred group of compounds that can be incorporated into the pharmaceutical compositions of the invention is the group of compounds wherein $R_1$ and $R_2$ are each independently selected from the group consisting of $(C_1–C_8)$alkyl and $(C_3–C_8)$cycloalkyl; $R_3$ is —C(=O)OR$_a$, —C(=O)SR$_a$, or —C(=O)OC(=O)R$_a$ wherein R$_a$ is $(C_1–C_8)$alkyl, $(C_2–C_8)$alkenyl, $(C_2–C_8)$alkynyl, $(C_3–C_8)$ cycloalkyl, aryl, aryl$(C_1–C_8)$alkyl, aryl$(C_1–C_8)$alkenyl, or aryl$(C_1–C_8)$alkynyl; and L is a covalent bond, $(C_1–C_6)$ alkylene, $(C_2–C_6)$alkenylene, or $(C_2–C_6)$alkynylene.

In another embodiment, a preferred group of compounds is the group of compounds wherein $R_1$ and $R_2$ are each independently isopropyl, 2-butyl, 2-pentyl, 3-pentyl, 2-hexyl, 3-hexyl, or $(C_3–C_6)$cycloalkyl; $R_3$ is —C(=O)OR$_a$ wherein R$_a$ is $(C_1–C_8)$alkyl, $(C_2–C_8)$alkenyl, $(C_2–C_8)$ alkynyl, $(C_3–C_8)$cycloalkyl, aryl, aryl$(C_1–C_8)$alkyl, aryl $(C_1–C_8)$alkenyl, or aryl$(C_1–C_8)$alkynyl; and L is methylene, ethylene, vinylene, propylene, allylene, butylene, pentylene, or hexylene.

A preferred group of compounds of formula (I) is the group of compounds wherein the group —L—$R_3$ is attached to the phenyl ring of formula (I) at the position ortho to the hydroxy group.

Another preferred group of compounds of formula (I) is the group of compounds wherein the group —L—$R_3$ is attached to the phenyl ring of formula (I) at the position para to the hydroxy group.

A preferred group of compounds of formula (II) is the group of compounds wherein the group —L—$R_3$ is attached to the phenyl ring of formula (II) at the position para to the hydroxy group.

A preferred group of compounds of formula (III) is the group of compounds wherein $R_3$ is —C(=O)OR$_a$.

The invention also provides a compound of formula (X):

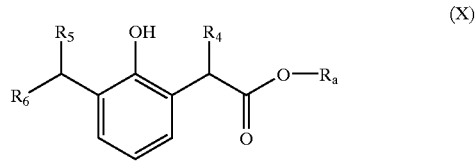

wherein $R_4$ is $(C_1–C_5)$alkyl, $(C_2–C_5)$alkenyl, or $(C_2–C_5)$alkynyl;

$R_5$ is $(C_1–C_6)$alkyl, $(C_3–C_8)$cycloalkyl, or $(C_3–C_8)$ cycloalkyl $(C_1–C_6)$alkyl; and $R_6$ is methyl;

or $R_5$ and $R_6$ together with the carbon atom to which they are attached form a $(C_3–C_8)$cycloalkyl; and R$_a$ is $(C_1–C_8)$alkyl, $(C_2–C_8)$alkenyl, $(C_2–C_8)$alkynyl or $(C_3–C_8)$cycloalkyl.

A preferred group of compounds of formula (X) is the group of compounds wherein $R_4$ is selected from $(C_1-C_5)$ alkyl; and $R_5$ is selected from $(C_1-C_5)$alkyl; or $R_5$ and $R_6$ together with the carbon atom to which they are attached form a $(C_3-C_6)$cycloalkyl; and $R_a$ is $(C_1-C_8)$alkyl.

A preferred group of compounds of formula (X) is the group of compounds wherein $R_4$ is methyl or ethyl; and $R_5$ is independently methyl or ethyl; or $R_5$ and $R_6$ together with the carbon atom to which they are attached form a $(C_{3-6})$ cycloalkyl; and $R_a$ is ethyl, propyl, isopropyl or 2-butyl.

Another preferred group of compounds of formula (X) is the group of compounds wherein $R_4$ and $R_5$ together with the carbon atom to which they are attached form a $(C_3-C_6)$ cycloalkyl.

Preferred compounds of formula (X) include the following:

6-isopropyl-2-(1-ethoxycarbonylethyl)-phenol;
6-isopropyl-2-(1-propoxycarbonylethyl)-phenol;
6-isopropyl-2-(2-propoxycarbonylethyl)-phenol;
6-isopropyl)-2-(1-ethoxycarbonyl-2-propyl)-phenol;
6-isopropyl-2-(1-propoxycarbonyl-2-propyl)-phenol;
6-isopropyl-2-(2-propoxycarbonyl-2-propyl)-phenol;
6-(2-butyl)-2-(1-ethoxycarbonylpropyl)-phenol;
6-(2-butyl)-2-(1-propoxycarbonylpropyl)-phenol;
6-(2-butyl)-2-(2-propoxycarbonylpropyl)-phenol;
6-(2-butyl)-2-(1-ethoxycarbonylethyl)-phenol;
6-(2-butyl)-2-(1-propoxycarbonylethyl)-phenol; and
6-(2-butyl)-2-(2-propoxycarbonylethyl)-phenol.

Another preferred group of compounds of formula (I) that can be incorporated in the pharmaceutical compositions of the invention is the group of compounds of formula (X).

Processes for preparing the compounds described herein are provided as further embodiments of the invention and are illustrated by the following procedures in which the meanings of the generic radicals are as given above unless otherwise qualified. Accordingly, the invention provides a method for preparing a phenol of formula (II) wherein L is a covalent bond and $R_3$ is a 4-methoxycarbonyl group, comprising treating a corresponding phenol wherein —L—$R_3$ is absent with carbontetrachloride and a copper catalyst in the presence of methanol and an suitable base (e.g., NaOH), for example, as described in example 1. The invention also provides a method for preparing a compound of formula (I, II, III, or IV), comprising deprotecting a corresponding protected phenol of formula (VI, VII, VIII, or IX) wherein $R_x$ is a suitable protecting group (such as for example methyl, benzyl or acetate), for example, as described in examples 2 and 3.

An intermediate useful for preparing a compound of formula (I) is a corresponding protected ether of formula (VI):

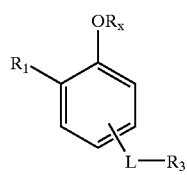

(VI)

wherein $R_1$, L, and $R_3$ have any of the values, specific values or preferred values described herein; and wherein $R_x$ is a suitable protecting group (e.g. methyl, benzyl or acetate). Suitable hydroxy protecting groups are well known in the art, for example, see Greene, T. W.; Wutz, P. G. M. "Protecting Groups In Organic Synthesis" second edition, 1991, New York, John Wiley & sons, Inc.

Another intermediate useful for preparing a compound of formula (II) is a corresponding protected ether of formula (VII):

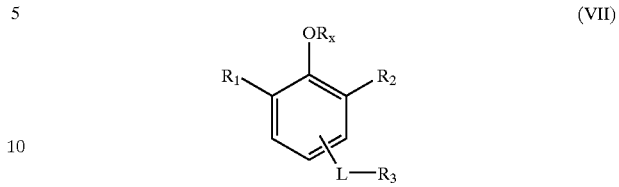

(VII)

wherein $R_1$, $R_2$, L, and $R_3$ have any of the values, specific values or preferred values described herein; and wherein $R_x$ is a suitable protecting group (e.g. methyl, benzyl or acetate).

An intermediate useful for preparing a compound of formula (III) is a corresponding protected ether of formula (VIII):

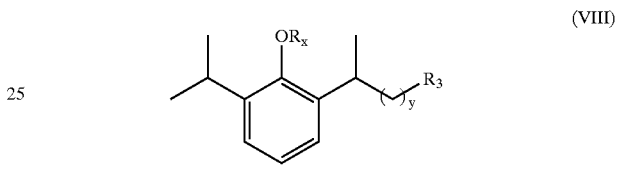

(VIII)

wherein $R_3$ has any of the values, specific values or preferred values described herein; y is 0, 1, 2, 3, 4, 5, or 6; and wherein $R_x$ is a suitable protecting group (e.g. methyl or benzyl).

An intermediate useful for preparing a compound of formula (IV) is a corresponding protected ether of formula (IX):

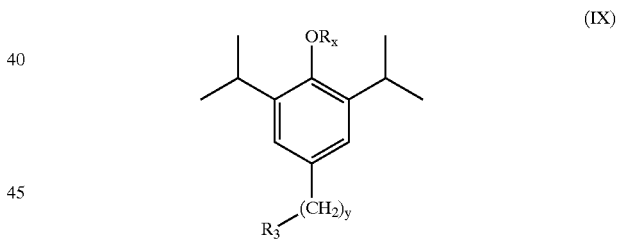

(IX)

wherein $R_3$ has any of the values, specific values or preferred values described herein; y is 0, 1, 2, 3, 4, 5, or 6; and wherein $R_x$ is a suitable protecting group (e.g. methyl or benzyl).

An intermediate useful for preparing a compound of formula (X) is a corresponding benzofuran of formula (A):

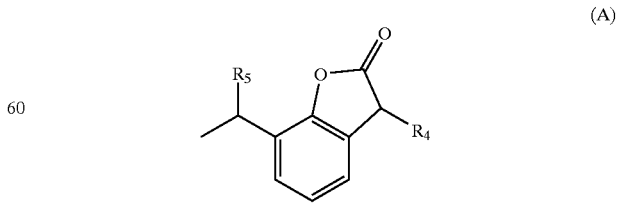

(A)

wherein $R_4$ and $R_5$ have any of the values, specific values or preferred values described herein.

Another intermediate useful for preparing a compound of formula (X) is a compound of formula (B):

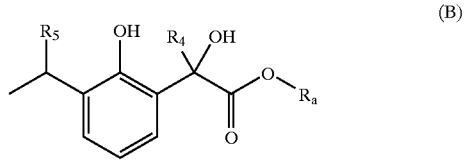

(B)

wherein $R_4$, $R_5$, and $R_a$ have any of the values, specific values or preferred values described herein.

In cases where active compounds are sufficiently basic or acidic to form stable nontoxic acid or base salts, administration of the compounds as salts can be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts can also be formed, including chloride, sulfate, nitrate, bicarbonate, and carbonate salts.

Pharmaceutically acceptable salts can be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formulae (I) and (II) can be formulated as pharmaceutical compositions and administered to a mammalian host, such as a human patient in a variety of forms adapted to the chosen route of administration, i.e., parenterally, by intravenous, intramuscular, topical or subcutaneous routes; or orally.

Active compounds described herein are typically formulated as pharmaceutical compositions which are suitable for intravenous administration. Like propofol, the active compounds described herein are relatively insoluble in water. Thus, for intravenous administration, the compounds of the invention are typically formulated in aqueous media using water-immiscible solvents, solubilizers, emulsifiers, surfactants or other solubilizing agents. Some emulsifiers are variously termed surfactants in the literature. Individual formulations may include one or more additional components such as stabilizers, tonicity modifiers, bases or acids to adjust pH, and solubilizers. The formulations can also optionally contain a preservative, such as ethylenediaminetetraacetic acid (EDTA) or sodium metabisulfate, to prevent the growth of microorganisms. Of course, any material used in preparing any unit dosage form should be pharmaceutically acceptable and substantially non-toxic in the amounts employed.

A wide range of water-immiscible solvents can be used in the compositions of the present invention. The water-immiscible solvent can be a vegetable oil, for example soybean, safflower, cottonseed, corn, sunflower, arachis, castor, palm or olive oil. Preferably, the vegetable oil is soybean oil. Alternatively, the water-immiscible solvent is an ester of a medium or long-chain fatty acid, for example, a mono-, di-, or triglyceride; or is a chemically modified or manufactured material such as ethyl oleate, isopropyl myristate, isopropyl palmirate, a glycerol ester, polyoxyl, or hydrogenated castor oil. The water-immiscible solvent can also be a marine oil, for example cod liver or another fish-derived oil. Suitable solvents also include fractionated oils, for example, fractionated coconut oil or modified soybean oil. Furthermore, the compositions of the present invention can comprise a mixture of two or more of the above water-immiscible solvents.

The compositions can also comprise an emulsifier. Suitable emulsifiers include synthetic non-ionic emulsifiers, for example ethoxylated ethers and esters polypropylene-polyethylene block co-polymers; and phospholipids for example, naturally-occurring phospholipids, such as egg and soya phospholipids and modified or artificially manipulated phospholipids (for example prepared by physical fractionation and/or chromatography), or mixtures thereof. Preferred emulsifiers are egg phospholipids, such as lecithin, and soya phospatides. Egg yolk phospholipids are principally composed of phosphatidylcholine and phosphatidylethanolamine. Lecithin, which is classified as a phosphatidylcholine, and which may be derived from egg yolk or soybean oil, is another commonly used emulsifier.

The pharmaceutical formulations can also include stabilizing agents, which can alternatively be considered as co-emulsifiers. Anionic stabilizers include phosphatidylethanolamines, conjugated with polyethylene glycol, (PEG-PE) and phosphatidylglycerols, a specific example of which is dimyristolphosphatidylgylcerol (DMPG). Additional examples of useful stabilizers include oleic acid and its sodium salt, cholic acid and deoxycholic acid and their respective salts, cationic lipids such as stearylamine and oleylamine, and 3β-[N-(N',N'-dimethylaminoethane)carbamoyl]cholesterol (DC-Chol).

The pharmaceutical compositions of the invention can be made isotonic with blood by the incorporation of a suitable tonicity modifier. Glycerol is most frequently used as a tonicity modifier. Alternative tonicity modifying agents include xylitol, mannitol, and sorbitol. The pharmaceutical compositions are typically formulated to be at physiologically neutral pH, typically in the range 6.0–8.5. The pH can be adjusted by the addition of base, for example NaOH or $NaHCO_3$, or in some cases acid, such as HCl.

Pharmaceutically safe oil-water emulsions comprising a vegetable oil, a phosphatide emulsifier, typically egg lecithin or soybean lecithin, and a tonicity modifier are provided commercially for parenteral nutrition, for example, under the tradenames Liposyn® II and Liposyn® III (Abbott Laboratories, North Chicago, Ill.) and Intralipid® (Fresenius Kabi AB, Uppsala, Sweden.) The compounds described herein can be incorporated in these or other similar oil-water emulsions.

A compound of the invention can also be formulated in a triglyceride comprising esters of at least one medium chain length ($C_6$–$C_{12}$) fatty acid. Preferably the triglyceride comprises an ester of a $C_8$–$C_{10}$ fatty acid. Triglycerides suitable for formulating a compound of the invention are provided under the tradename Miglyol® by Condea Chemie GmbH (Witten, Germany). In particular, Miglyol® 810 or 812 (caprylic ($C_{10}$)/capric ($C_8$) glyceride) are useful for formulation of the present compounds. For example, as detailed in Injection 11 of Example 15 below, Miglyol® 810 is beneficially used as the oil phase of a formulation that includes egg yolk phosphatides as the emulsifier, DMPG as an anionic stabilizer, and glycerol as the tonicity modifier.

Additionally, the compounds described herein can be substituted for propofol in any of the propofol compositions known to the art. For example, suitable sterile pharmaceutical compositions of propofol and methods for their administration are generally described in U.S. Pat. Nos. 4,056,635; 4,452,817, 4,798,846 and 5,714,120.

Another suitable pharmaceutical composition for the administration of propofol, described in U.S. Pat. Nos. 6,140,373 and 6,140,374, is an oil-in-water emulsion formulation having as an antimicrobial agent, a member selected from the group consisting of benzyl alcohol; benzyl alcohol and disodium ethylenediamine tetraacetate; benzyl alcohol and ethylene diamine tetraacetic acid; benzethonium chloride; and benzyl alcohol and sodium benzoate.

Another suitable pharmaceutical composition for the administration of propofol, described in U.S. Pat. Nos.

5,637,625 and 5,908,869, comprises a sterile, pyrogen-free oil-in-water emulsion containing soybean oil dispersed in water and stabilized by lecithin phospholipids, and further comprises an amount of edetate to inhibit the growth of gram-positive and gram-negative bacteria.

A further suitable pharmaceutical composition for the administration of propofol, described in U.S. Pat. No. 5,637,625, is an oil-free formulation in which the propofol is dispersed in water as micro-droplets with a diameter generally less than 1 micron, having a phospholipid or monoglyceride outer covering.

Another suitable pharmaceutical composition for the administration of propofol, described in U.S. Pat. No. 6,100,302, consists of phospholipid-coated microdroplets ranging from about 160 to about 200 nanometers in diameter. These microdroplets contain a sphere of propofol dissolved in a solvent, such as vegetable oil, surrounded by a stabilizing layer of a phospholipid, and suspended in a pharmaceutical acceptable injectable carrier.

A further suitable pharmaceutical composition for the administration of propofol, described in U.S. Pat. No. 5,962,536, uses N-methylpyrrolidone, 2-pyrrolidone or other physiologically acceptable co-solvents as a solvent for the solubilization of propofol.

In yet another alternative, the present compounds can be formulated using a solubilizer, for example, hydroxypropyl β-cyclodextrin, to form an inclusion complex.

In yet another alternative, the present compounds can be systemically administered orally as tablets, capsules, suspensions, syrups, and the like or as a systained-release preparation, in combination with a pharmaceutically acceptable vehicle such as an inert diluent or an assimilable edible carrier. Oral pharmaceutical formulations of the present compounds can also include binders, excipients, a disintegrating agent, a lubricant, sweetening or flavoring agents, preservatives, or other pharmaceutically acceptable ingredients as known in the pharmaceutical arts.

Still other suitable formulations for use in the present invention can be found in Remington's Pharmaceutical Sciences, Mace Publishing Company, Philadelphia, Pa. 17th ed. (1985).

Compounds of the present invention can be used for the induction and/or maintenance of general anesthesia, for example to permit the performance of surgery or other painful procedures; for the initiation and/or maintenance of sedation with patients spontaneously breathing, to which the term Monitored Anesthesia Care (MAC) sedation may be applied; and for the induction and/or maintenance of sedation for intubated, mechanically ventilated patients.

The compounds of the invention can also be administered in combination with other therapeutic agents, such as, for example, other anesthetics or sedatives, or analgesics (e.g. an opioid such as the µ-opioid agonist remifentanil, fentanyl, sulfentanil, or alfentanil). Accordingly, the compositions of the invention can optionally further comprise another therapeutic agent, for example, an anesthetic, sedative, or analgesic. Similarly, the therapeutic methods of the invention can also optionally comprise administering another therapeutic agent (e.g. an anesthetic, sedative, or analgesic) to the mammal.

Alternatively, a continuous infusion of a compound of the present invention can be used to maintain anesthesia or sedation following induction with another sedative hypnotic agent. Or, in yet another alternative protocol, a bolus dose of the present compound to induce anesthesia or sedation can be followed by infusion of a different sedative hypnotic agent.

The amount of an active compound required for use in treatment will vary with the route of administration and the age and condition of the patient, and will be ultimately at the discretion of the attendant physician or clinician.

Useful dosages of the substituted phenol compounds of the invention can be determined by comparing their in vitro activity, and in vivo activity in animal models. Methods for the extrapolation of effective dosages in mice, and other animals, to humans are known to the art; for example, see U.S. Pat. No. 4,938,949. Such compositions and preparations should contain at least 0.1% of active compound. The percentage of the compositions and preparations can, of course, be varied and can conveniently be between about 1% to about 60% of the weight of a given unit dosage form. The amount of active compound in such therapeutically useful compositions is such that an effective dosage level will be obtained.

In general, the substituted phenol compounds of the invention can be administered as an initial bolus induction dose followed by a continuous infusion of the compound at a rate that is sufficient to achieve and maintain the level of anesthesia or sedation desired. For example, a suitable bolus dose will typically be in the range of from about 0.1 to about 50 mg/kg, preferably about 0.5 to about 20 mg/kg, and more preferably about 1 to about 10 mg/kg. The rate of infusion will typically be in the range from about 5 to about 2000 µg/kg/min, preferably about 10 to about 1000 µg/kg/min, and more preferably about 50 to about 500 µg/kg/min. Target blood levels during infusion will typically be, for example, in the range of from about 0.1 to about 50 µg/mL, preferably about 0.5 to about 20 µg/mL, and more preferably about 1.0 to about 10 µg/mL.

The in vitro stability of a compound in rat liver, skeletal muscle, and whole blood in comparison with two clinically used esterase substrates (esmolol and remifentanil) can be determined as described in Test A.

Test A: In vitro Stability in Rat Liver, Skeletal Muscle, and Whole Blood

Methods

Source of Enzyme

Liver and skeletal muscle tissue were harvested from rats sacrificed using $CO_2$ (dry ice). Tissues were homogenized in phosphate buffered saline at 4° C. and 20% homogenates were prepared (on a wet weight basis). Homogenates were aliquoted and frozen at −80° C. The total protein concentration in the homogenates was estimated using the bicinchoninic acid assay (Pierce). Whole blood was obtained by cardiac puncture and collected in vacutainer tubes containing sodium heparin to prevent coagulation. Fresh blood was used in the assay and was placed in ice until the time of assay.

Substrates

Esmolol was purchased as a 250 mg/mL solution (concentrated I.V. dosage form from Baxter) and diluted in sterile water to a concentration of 5 mM. Remifentanil was purchased as the I.V. dosage form which was a lyophilized powder. This was reconstituted in sterile water to a concentration of 5 mM. Solutions of the substituted phenol compounds (50 mM) were prepared in DMSO. All stock solutions were stored at −20° C. and their purity was established by HPLC.

Metabolism Assay

The stability of all compounds was studied at an assay concentration of 100 µM. For liver and skeletal muscle, the final assay protein concentration was 5 mg/mL and for blood metabolism, undiluted whole blood was used. Control incubations in the assay buffer (100 mM $KH_2PO_4$, pH 7.4) without any biological material were run in parallel to confirm chemical stability. The test compounds were spiked into the homogenates or whole blood in glass tubes (0.5 mL volume) and the proteins were immediately precipitated with the addition of twice the volume of ice-cold ethanol and vortex mixing. This constituted the zero time point. In identical 0.5 mL incubations, the compounds were incubated for 20 minutes at 37° C. prior to addition of the ethanol. For reactions in whole blood, a 3 minute reaction was also performed. To all tubes, 25 μl of a 4 mg/100 mL solution of 3-acetamidophenol was added as the internal standard and the contents were mixed by vortexing. The suspensions were centrifuged at 14,000 rpm and the supernatants were transferred to glass tubes and evaporated under a gentle stream of nitrogen. The residue was reconstituted in 0.2 mL of sterile water and 50 μl was analyzed by HPLC.

HPLC Method

A $C_{18}$, 5μ, 2×150 mm I.D (LUNA, Phenomenex) reverse-phase HPLC column was used and a gradient from 10% to 68% acetonitrile over 15 minutes followed by a 5 minute isocratic run at 10% acetonitrile was used. The mobile phase components contained 0.1% TFA. The analytes were monitored by UV detection at 214 nm.

Data Analysis

Concentrations of the substrate in incubates were measured as peak area ratios using the internal standard method and percent degradation was measured relative to the zero time values.

Results

The test compounds are typically stable in the incubation buffer at 37° C. for 20 minutes. Additionally, the substituted phenol compounds tested were found to be substrates for esterases in the rat. Typically, the substituted phenol compounds were completely metabolized to the corresponding acid after a 20 minute incubation with rat liver homogenate.

The in vitro affinity of substituted phenol compounds and their corresponding acid metabolites for the GABA receptor can be determined using competitive binding assays known in the art, as described for example in D. Sapp et al., *J. Pharmacol. Exp. Ther.,* 1992, 262, 801–807; A. Concas et al., *Eur. J. Pharmacol.,* 1994, 267, 207–213; A. Concas et al, *Brain Research,* 1991, 542, 225–232; and J. Hawkinson et al., *Mol. Pharmacol.,* 1994, 46, 977–985. A suitable competitive binding assay is described below in "Test B."

Test B: in vitro Competitive Binding Affinity Assay for the GABA Receptor

Methods

The assay was run on 100 μl scale by combining the following.

–25 μl [4×] cold ligand or buffer (Tris, HCl (50 mM) with KCL (150 mM at pH 7.4)
–25 μl [4×] [$^{35}$S] TBPS at 5 nM final concentration
–50 μl [2×] rat cortex membrane at 0.2 mg/mL final This mixture was incubated at room temperature for 90 minutes with shaking and filtered through a Packard 96 well GFB filter plate soaked with 0.1% BSA. The radioactivity on the resulting plate determined, and the ability of the test compound to inhibit TPBS binding was calculated.

Results

Representative substituted phenol compounds were found to bind to GABA receptors with affinities similar to propofol.

The ability of a compound to function as an anesthetic or a sedative can be determined using assays that are known in the art (for example see U.S. Pat. No. 5,908,869 or R. James and J. Glen, *J. Med Chem.,* 1980, 23, 1350–1357) or using the assay described in Test C below.

Test C: in vivo Assay to Measure Duration of Anesthesia

The following assay was used to determine whether the substituted phenol compounds (and their corresponding acid derivatives) produce anesthesia of short duration following administration via intravenous bolus administration and infusion in rats. Rats were dosed using formulations of from about 3 weight % to about 10 weight % active compound. The vehicle used in the initial studies was 10% cremophor EL/90% D5W (5% dextrose in distilled water). While this vehicle proved suitable for the experiments with bolus administration of the anesthetics, upon infusion some toxicity was observed (i.e., lethargy and sedation). As a result, 10% Liposyn III (an intravenous fat emulsion containing (per 100 mL) 10 g soybean oil, ≦1.2 g egg phosphatides and 25 g glycerol) became the vehicle of choice; it produced no such adverse effects in its own right and closely mimicked the vehicle used clinically for propofol.

Methods

Bolus Administration

Rats (adult male Sprague-Dawley) were placed in a perspex restrainer and injected (2 mL/kg over approximately 3 seconds) with the compound of interest via the tail vein. The time to onset of anesthesia (defined as a loss of righting reflex), duration of anesthesia (i.e., duration of loss of righting reflex) and behavioral recovery (i.e., duration of ataxia, sedation and/or lethargy following the return of the righting reflex) was recorded. Duration of anesthesia was measured by placing the rats ventral side uppermost following onset of anesthesia and the time until recovery of the righting reflex recorded using a stopclock. The depth of anesthesia was assessed intermittently by observing the magnitude of the withdrawal reflex to noxious pinch of the hindpaw. Behavioral recovery was assessed by visual observation. The compounds produced a dose-dependent loss of righting reflex. Doses of preferred compounds produced a 2 minute loss of righting reflex at 20 mg/kg or less.

Administration by Infusion

Rats (adult Sprague-Dawley) were placed in a perspex restrainer and anesthesia induced by bolus injection via the tail vein (1 mL/kg over approximately 3 seconds at a dose, estimated from the earlier bolus experiments, to produce anesthesia of approximately 2 minutes duration). Immediately after bolus administration, a 20 minute infusion, via the tail vein, was commenced (0.5 mL/kg/min at a half of the bolus dose/min). In some experiments, the initial infusion rate was maintained throughout, while in others, the rate was modified as necessary to maintain a consistent depth of anesthesia (as defined by moderate paw withdrawal in response to noxious pinch). Following completion of the infusion, duration of anesthesia (i.e., duration of loss of righting reflex) and behavioral recovery (i.e., duration of ataxia, sedation or lethargy following return of the righting reflex) was recorded.

Representative substituted phenol derivatives produced anesthesia following bolus administration. The corresponding acids failed to induce anesthesia. Preferred compounds of this invention maintained anesthesia when infused i.v. at doses of 10 mg/kg/min or less and maintained anesthesia for the duration of the i.v. infusion. Following termination of the 20 minute infusion, recovery of the righting reflex was rapid (<10 minutes). Recovery times matched those following bolus administration suggesting that there was little/no accumulation of the compounds over time.

The invention will now be illustrated by the following non-limiting Examples.

EXAMPLES

Example 1

4-Methoxycarbonyl-2,6diisopropylphenol

Carbon tetrachloride (28 mL) was added dropwise to a mixture of 2,6-diisopropylphenol (37.5 mL), copper powder (2 g), methanol (150 mL), and 40% aqueous solution of sodium hydroxide (150 mL), at 40–50° C. The reaction temperature was warmed to about 60° C., and the resulting mixture was allowed to stir for 4 hours. The mixture was poured into water and extracted with toluene (3×). The combined organics were washed (brine), dried over sodium sulfate and concentrated. Chromatography with ethyl ether-:hexanes as the eluent (gradient 5/95 to 8/92) provided material that precipitated as a white solid upon addition of hexane. The white solid was collected by filtration to provide the title compound (1.06 g); $^1$H-NMR(CDCl$_3$) δ=1.29 (d, 12H, CH(CH$_3$)$_2$), 3.16 (m, 2H, CH (CH$_3$)$_2$), 3.87 (S, 3H, OCH$_3$), 5.22 (S, 1H, OH), 7.78 (S, 2H, ArH).

Example 2

(E)-4-(2-Methoxycarbonylvinyl)-2,6-diisopropylphenol

Methyl 3-(3,5-diisopropyl-4-methoxyphenyl)acrylate (610 mg) and boron tribromide (10 mL) were combined in dichloromethane (10 mL) and the mixture was allowed to stir at 0° C. for 5 hours. The reaction was quenched with water and extracted with dichloromethane. The organics were washed (brine), dried (sodium sulfate), filtered, and condensed. Chromatography, with ethyl ether:hexane (gradient 10:90 to 20:80) as the eluent, provided material that was recrystallized from hexane to give the title compound as a white solid (420 mg); $^1$H-NMR (CDCl$_3$) δ=1.28 (d, 12H, CH(CH$_3$)$_2$), 3.16 (m, 2H, CH(CH$_3$)$_2$), 3.80 (S, 3H, OCH$_3$), 5.10 (S, 1H, OH), 6.32 (d, 2H, CH=CH), 7.24 (S, 2H, Ar—H), 7.66 (d, 2H, CH=CH).

The intermediate methyl 3-(3,5-diisopropyl-4-methoxyphenyl)acrylate was prepared as follows.

a. 4-Hydroxy-3,5-diisopropylbenzaldehyde. Formaldehyde (40%, 5.0 mL) and aqueous ammonium hydroxide (30%, 3.74 mL) were added to a solution of 2,6-diisopropylphenol (5.0 g) in glacial acetic acid (270 mL). After 24 hours on a stream bath, the solvents were evaporated under reduced pressure. The resulting material was dissolved in chloroform, washed with 5% aqueous sodium bicarbonate, dried (MgSO$_4$), filtered, and concentrated. Chromatography, with 10% ethyl acetate in hexanes as the eluent, provided the aldehyde (520 mg).

b. 3,5-diisopropyl-4-methoxybenzaldehyde. 4-Hydroxy-3,5-diisopropylbenzaldehyde (1.36 g), iodomethane (0.5 mL), and potassium carbonate (1.85 g) were combined in a solution of acetone (40 mL) and dimethyl formamide (10 mL). The reaction mixture was stirred at room temperature for 24 hours and concentrated. The resulting material was taken into diethyl ether, washed (brine), dried (sodium sulfate), filtered, and concentrated to give the methyl ether as a yellow oil (1.4 g).

c. Methyl 3-(3,5-diisopropyl-4-methoxyphenyl)acrylate. 3,5-diisopropyl-4-methoxybenzaldehyde (881 mg) was stirred with silica-gel (2.7 g) for about 10 minutes to get a free powder. Ph$_3$P=CHCOOCH$_3$ (1.7 g) was added, followed by 10 mL of hexane. The reaction mixture was heated at 50° C. for 24 hours, and the resulting mixture was loaded on a silica-gel column. Chromatography, with diethyl ether:hexane (10:90) as the eluent, provided the ester (944 mg).

Example 3

2,6-Diisopropyl-4-methoxycarbonylmethylphenol

To a solution of methyl 3,5-diisopropyl-4-methoxyphenylacetate (100 mg) in dichloromethane (12 mL) at −78° C. was added a solution of boron tribromide (0.57 mL) in dichloromethane. The reaction mixture was stirred at −78° C. for 1 hour and at 0° C. for 1 hour, quenched by water, and extracted with dichloromethane. The combined organics were washed (brine), dried (MgSO$_4$), filtered, and concentrated. Purification by preparative thin layer chromatography, with ethyl acetate:hexane:acetic acid (90:9:1) gave the title compound (24 mg); $^1$H-NMR (CDCl$_3$) δ=1.25 (d, 12H, CH(CH$_3$)$_2$), 3.15 (m, 2H, CH(CH$_3$)$_2$), 3.55 (S, 2H, CH$_2$), 3.70 (S, 3H, OCH$_3$), 6.98 (S, 2H, ArH)

The intermediate methyl 3,5-diisopropyl-4-methoxyphenylacetate was prepared as follows.

a. 2,6-Diisopropyl-1-(2-propenyloxy)benzene. 2,6-diisopropylphenol (12 g) was dissolved in dimethylformamide (200 mL) and sodium hydride (5.4 g) was added. The mixture was stirred at 0° C. for 5 minutes and at ambient temperature for another 15 minutes. The solution was cooled to 0° C., allyl iodide (9.3 mL) was added, and the mixture was stirred at for 15 minutes. The mixture was allowed to warm to ambient temperature and was stirred for another 2 hours. Saturated aqueous ammonium chloride was added and the mixture was extracted with ethyl acetate. The combined organics were dried (MgSO$_4$), filtered through a pad of silica gel, and concentrated to provide the ether (16 g).

b. 4-Allyl-2,6-diisopropylphenol. 2,6-Diisopropyl-1-(2-propenyloxy)benzene (1.5 g) and N,N-dimethylpropyleneurea (14 mL) were combined and heated to 165° C. in a sealed tube for 4 hours. The reaction mixture was poured into ether and the ether was washed with water, dried (sodium sulfate), filtered and condensed. Chromatography with ether:hexanes (gradient 2:98 to 5:98) provided the phenol, which was used without further purification.

c. 4-Allyl-2,6-diisopropyl-1-methoxybenzene. 4-Allyl-2,6-diisopropylphenol (9.2 g) and potassium carbonate (0.7 g) were combined in dimethylformamide (60 mL) and iodomethane (3.2 mL) was added. After 2 hours, additional potassium carbonate (2 g) and iodomethane (1 mL) were added. After 12 hours, the reaction mixture was partitioned between ethyl acetate and water. The organic phase was washed with saturated aqueous sodium bicarbonate and brine, dried (MgSO$_4$), filtered through a thin pad of silica gel, and concentrated to give the methyl ether as a light yellow oil (10.7 g).

d. 4–Carboxymethyl-2,6-diisopropyl-1-methoxybenzene. Benzyltriethylammonium bromide (360 mg) and potassium permanganate (2.6 g) were added to a solution of 4-allyl-2,6-diisopropyl-1-methoxybenzene (1.5 g) at 0° C. The reaction mixture was stirred vigorously for 1 hour and was warmed to 10° C. and stirred for an additional hour. A 5% solution of Na$_2$S$_2$O$_5$ in water was added, followed by 1 N HCl to make the mixture acidic. The mixture was washed twice with dichloromethane and the combined organics were dried (MgSO$_4$), filtered, and concentrated. Chromatography, with 10% ethyl acetate in hexanes (with acetic acid) as the eluent, provided the acid.

e. 3,5-Diisopropyl-4-methoxyphenylacetate. 4–Carboxymethyl-2,6-diisopropyl-1-methoxybenzene (200 mg) was combined with 2 drops concentrated sulfuric acid in methanol (2.5 mL) and the mixture was heated to 80° C. for 2 hours. The mixture was concentrated and purified by chromatography with 5% EtOAc in hexanes (with 1% acetic acid) as the eluent, to provide the methyl ester (100 mg).

Example 4

4-(2-Methoxycarbonylethyl)-2,6-diisopropylphenol 4-(2-Methoxycarbonylvinyl)-2,6-diisopropylphenol (Example 1, 350 mg) was dissolved in a solution of ethyl acetate (10 mL) and methanol (10 mL) and hydrogenated at 35 psi over palladium on carbon (Pd/C) for 24 hours. The resulting mixture was filtered and the filtrate was concentrated to provide the title compound; $^1$H-NMR (CDCl$_3$) δ=1.27 (d, 12H, CH(CH$_3$)$_2$), 2.60 (t, 2H, CH$_2$), 2.87 (t, 2H, CH$_2$), 3.13 (m, 2H, CH(CH$_3$)$_2$), 3.68 (S, 3H, OCH$_3$), 6.87 (S, 2H, ArH).

Example 5

7-isopropyl-2-methyl-benzofuran-3-one

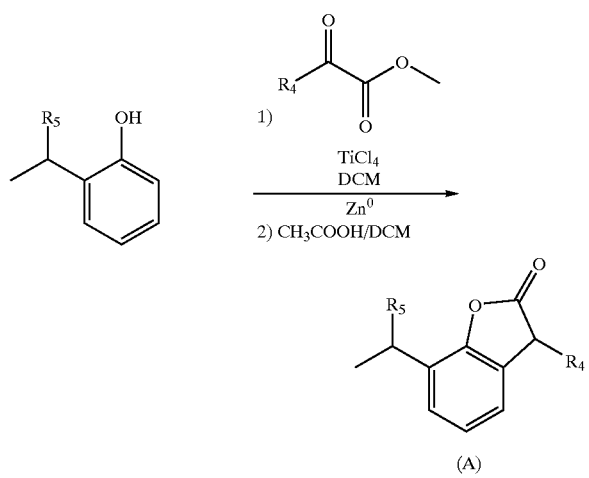

2-isopropylphenol (10 mL) was dissolved in anhydrous methylene chloride (150 mL), methyl pyruvate (7.3 mL) was added and the solution was cooled in an ice bath and flushed with nitrogen. A 1.0 M solution of titanium (IV) chloride in methylene chloride (72 mL) was added dropwise over 1 hour via addition funnel while still under nitrogen. The reaction was stirred for another 1 hour after completion of addition until reaction was complete.

The mixture was then poured into a suspension of zinc (0) (20 g) in a solution of acetic acid (50 mL) and methylene chloride (100 mL). This mixture was then heated slowly to 90° C. and the methylene chloride was distilled off, the mixture was heated for another 30 minutes after distillation was finished and reaction was complete.

Once cooled, the mixture was decanted into ether (400 mL) and washed with distilled water (4×200 mL). The organic was collected and neutralized with saturated sodium bicarbonate solution to neutral pH, then washed with brine (1x) and dried over magnesium sulphate, and concentrated under vacuum yielding crude product (12.7 g).

Chromatography with 5% ethyl acetate: hexanes as the eluent provided a colourless oil of 7-isopropyl-2-methyl-benzofuran-3-one (10.7 g). (Intermediate (A), wherein $R_5$ and $R_4$=methyl). $^1$H-NMR(DMSO) δ=1.15 (d of d, 6H, $CH_3$(i-Pr)), 1.35 (d, 3H, $CH_3$), 3.00 (m, 1H, CH(i-Pr)), 3.90 (q, 1H, CH), 7.04 (t, 1H, ArH), 7.14 (d, 2H, ArH).

Example 6

7-sec-butyl-2-methyl-benzofuran-3-one

Using the procedure described in Example 5, substituting 2-sec-butylphenol (10 mL) for 2-isopropylphenol as the starting material, a colourless oil of intermediate 7-sec-butyl-2-methyl-benzofuran-3-one was synthesized. (Intermediate (A), wherein $R_5$=ethyl; $R_4$=methyl). $^1$H-NMR (DMSO) δ=0.65 (t, 3H, $CH_3$), 1.02 (d, 3H, $CH_3$), 1.43 (d, 3H, $CH_3$), 1.59 (m, 2H, $CH_2$), 2.75 (m, 1H, CH(sec)), 3.97 (m, 1H, CH), 7.00–7.20 (m, 3H, ArH).

Example 7

2-ethyl-7-isopropyl-benzofuran-3-one

Using the procedure described in Example 5, substituting reagent methyl 2-ketobutyrate (8.0 mL) for methyl pyruvate, provided a colourless oil of 2-ethyl-7-isopropyl-benzofuran-3-one. (Intermediate (A), wherein $R_5$=methyl; $R_4$=ethyl). $^1$H-NMR(DMSO) δ=0.75 (t, 3H, $CH_3$), 1.14 (d of d, 6H, $CH_3$(i-Pr)), 1.87 (m, 2H, $CH_2$), 3.00 (m, 1H, CH(i-Pr)), 3.90 (t, 1H, CH), 7.05 (t, 1H, ArH), 7.14 (d, 2H, ArH).

Example 8

7-sec-butyl-2-ethyl-benzofuran-3-one

Using the procedure described in Example 6, substituting reagent methyl 2-ketobutyrate (8.0 mL) for methyl pyruvate, a colourless oil of intermediate 7-sec-butyl-2-ethyl-benzofuran-3-one was obtained. (Intermediate (A), wherein $R_5$=ethyl; $R_4$=ethyl).

Example 9

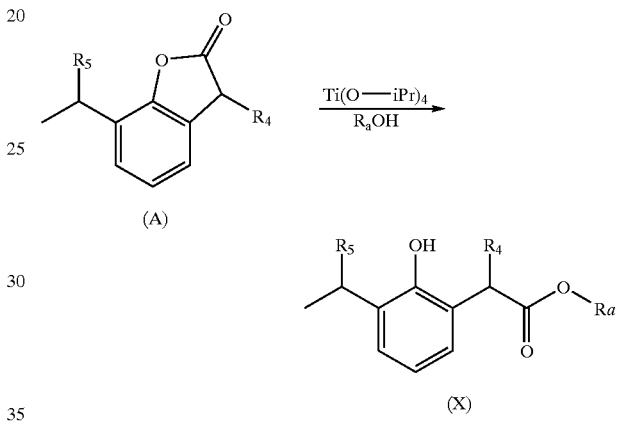

(a) 6-isopropyl-2-(1-ethoxycarbonylethyl)-phenol 7-isopropyl-2-methyl-benzofuran-3-one, synthesized in Example 5, (3.8 g) was dissolved in anhydrous ethanol (200 mL) and cooled in an ice bath under nitrogen before addition of titanium (IV) isopropoxide (6.25 mL). The reaction was then heated to 90° C. for a few hours. Once cooled, the reaction mixture was poured into hexanes and washed with saturated ammonium chloride solution, brine, dried over magnesium sulphate and concentrated under vacuum. Chromatography with 2% ethyl acetate: hexanes as the eluent provided a colourless oil of 6-isopropyl-2-(1-ethoxycarbonylethyl)-phenol, alternatively known as 2-(2-hydroxy-3-isopropyl-phenyl)-propionic acid ethyl ester. (A compound of formula (X) wherein $R_5$ and $R_4$=methyl; $R_a$=ethyl). ($^1$H-NMR(DMSO) δ=1.02 (m, 9H, $CH_3$), 1.22 (d, 3H, $CH_3$), 3.19 (m, 1H, CH), 3.95 (m, 3H, CH+$CH_2$O), 6.68 (t, 1H, ArH), 6.81 (d, 1H, ArH), 6.98 (d, 1H, ArH), 8.28 (s, 1H, Ar—OH).

(b) 6-isopropyl-2-(1-propoxycarbonylethyl)-phenol, alternatively known as 2-(2-hydroxy-3-isopropyl-phenyl)-propionic acid propyl ester, is obtained by substituting anhydrous propanol for ethanol using the procedure described in Example 9(a) above. (A compound of formula (X) wherein $R_5$ and $R_4$=methyl; $R_a$=propyl).

(c) 6-isopropyl-2-(2-propoxycarbonylethyl)-phenol, alternatively known as 2-(2-hydroxy-3-isopropyl-phenyl)-propionic acid isopropyl ester, is obtained by using the procedure described in Example 9(a) above, and substituting anhydrous iso-propanol for ethanol. (A compound of formula (X) wherein $R_5$ and $R_4$=methyl; $R_a$=isopropyl).

Example 10

6-(2-sec-butyl)-2-(1-ethoxycarbonylethyl)-phenol

Using the procedure described in Example 9(a) above, and starting with 7-sec-butyl-2-methyl-benzofuran-3-one, synthesized in Example 6, a colourless oil of the title compound, alternatively known as 2-(3-sec-butyl-2-hydroxy-phenyl)-propionic acid ethyl ester, was obtained. (A compound of formula (X) wherein $R_5$=ethyl; $R_4$=methyl; $R_a$=ethyl). $^1$H-NMR(DMSO) δ=0.70 (q, 3H, $CH_3$), 1.02 (m, 6H, $CH_3$), 1.22 (d, 3H, $CH_3$), 1.41 (m 2H, $CH_2$), 3.00 (q, 1H, CH), 3.95 (m, 3H, CH+$CH_2$O), 6.68 (t, 1H, ArH), 6.81 (d, 1H, ArH), 6.95 (d, 1H, ArH), 8.25 (s, 1H, Ar—OH).

Example 11

6-isopropyl-2-(1-ethoxycarbonylpropyl)-phenol

Using the method described in Example 9(a) above, and starting with 2-ethyl-7-isopropyl-benzofuran-3-one synthesized in Example 7, a colorlous oil of the title compound, alternatively known as 3-(2-hydroxy-3-isopropyl-phenyl)-butyric acid ethyl ester, was obtained. (A compound of formula (X) wherein $R_5$=methyl; $R_4$=ethyl; $R_a$=ethyl).

Example 12

6-isopropyl-2-(1-ethoxycarbonyl-1-hydroxyethyl)-phenol

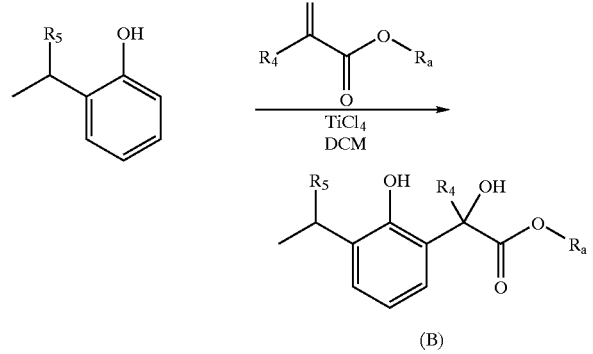

2-isopropylphenol (10 mL) was dissolved in anhydrous methylene chloride (150 mL); ethyl pyruvate (8.3 mL) was added and the solution was cooled in an ice bath and flushed with nitrogen. A solution of titanium (IV) chloride (8.2 mL) in methylene chloride (~75 mL) was prepared and added dropwise over 1 hour via addition funnel while still under nitrogen. The reaction was stirred for another 1–2 hours after completion of addition until reaction was complete. The mixture was diluted with ether (400 mL) and washed with distilled water (4×200 mL), brine (1×), dried over magnesium sulphate, and concentrated under vacuum yielding a yellow oil as crude product of the title compound, alternatively known as 2-hydroxy-2-(2-hydroxy-3-isopropyl-phenyl)-propionic acid ethyl ester (18.9 g). (Intermediate (B) where $R_5$=$R_4$=methyl and $R_a$=ethyl). $^1$H-NMR(DMSO) δ=0.99–1.06 (m, 9H, $CH_3$), 1.59 (s, 3H, $CH_3$), 3.15 (m, 1H, CH(i-Pr)), 3.99 (m, 2H, $CH_2$O), 6.72 (t, 1H, ArH), 7.00 (d, 2H, ArH), 9.03 (s, 1H, ArOH).

Using the procedure described above and substituting 2-sec-butylphenol for 2-isopropylphenol, 6-(2-sec-butyl)-2-(1-ethoxycarbonyl-1-hydroxyethyl)-phenol (Intermediate (B) where $R_5$=ethyl; $R_4$=methyl and $R_a$=ethyl) is obtained.

Using the procedure described above and substituting methyl-2-ketobutyrate for ethyl pyruvate, 6-isopropyl-2-(1-ethoxycarbonyl-1-hydroxypropyl)-phenol (Intermediate (B) wherein $R_5$=methyl; $R_4$=ethyl and $R_a$=ethyl) is obtained.

Example 13

6-isopropyl-2-(1-ethoxycarbonylethyl)-phenol

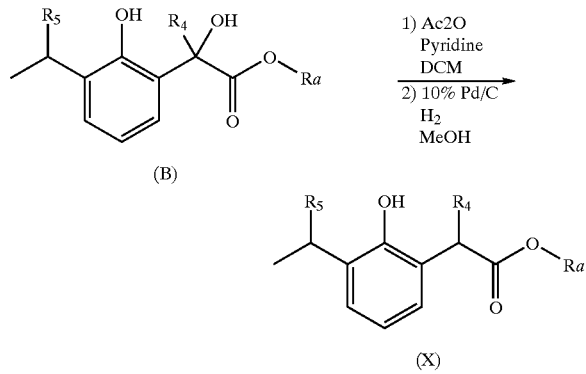

6-isopropyl-2-(1-ethoxycarbonyl-1-hydroxyethyl)-phenol, synthesized in Example 12, (18.9 g) was dissolved in anhydrous methylene chloride (250 mL) and cooled in an ice bath under nitrogen before addition of pyridine (36 mL). Acetic anhydride (28 mL) was then added and the reaction stirred overnight while slowly warming to room temperature. The solution was diluted with diethyl ether and washed with saturated ammonium chloride solution, 1N HCl, brine, dried over magnesium sulphate and concentrated under vacuum to give a yellow oil as crude product material.

The crude product material was dissolved in methanol (250 mL), 10% Pd/C (2.1 g) wet with distilled water; and methanol was added and the mixture was hydrogenated overnight at 30 psi hydrogen with shaking. The Pd/C was removed by filtration and rinsed with methanol and solvent was removed under vacuum yielding a yellow oil as crude product (19 g).

Chromatography of the crude product with 1% ethyl acetate: hexanes as the eluent provided a light yellow oil of the title compound, alternatively known as 2-(2-hydroxy-3-isopropyl-phenyl)-propionic acid ethyl ester (3.8 g). (A compound of formula (X) wherein $R_5$=$R_4$=methyl and $R_a$=ethyl). $^1$H-NMR(DMSO) δ=1.02–1.07 (m, 9H, $CH_3$), 1.23 (d, 3H, $CH_3$), 3.20 (m, 1H, $CH_3$(i-Pr)), 3.97 (m, 3H, CH, $CH_2$O), 6.72 (t, 1H, ArH), 6.81 (d, 1H, ArH), 6.96 (d, 1H, ArH), 8.28 (s, 1H, ArOH).

Example 14

Following the procedures described in Examples 5–13, the following compounds of formula (X) can be prepared.

TABLE I

| $R_5$ | $R_4$ | $R_a$ | Compound |
|---|---|---|---|
| ethyl | methyl | propyl | 6-(2-sec-butyl)-2-(1-propoxycarbonylethyl)-phenol |
| ethyl | methyl | isopropyl | 6-(2-sec-butyl)-2-(2-propoxycarbonylethyl)-phenol |
| methyl | ethyl | propyl | 6-isopropyl-2-(1-propoxycarbonylpropyl)-phenol |
| methyl | ethyl | isopropyl | 6-isopropyl-2-(2-propoxycarbonylpropyl)-phenol |
| ethyl | ethyl | ethyl | 6-(2-sec-butyl)-2-(1-ethoxycarbonylpropyl)-phenol |
| ethyl | ethyl | propyl | 6-(2-sec-butyl)-2-(1-propoxycarbonylpropyl)-phenol |
| ethyl | ethyl | isopropyl | 6-(2-sec-butyl)-2-(2-propoxycarbonylpropyl)-phenol |

Example 15

The following illustrates representative pharmaceutical dosage forms, containing a substituted phenol ring linked to a reactive functional group ('Active Compound'), for therapeutic or prophylactic use in humans and animals.

|  | wt % |
|---|---|
| (i) Injection 1 | |
| 'Active Compound' | 2.0 |
| soybean oil | 10.0 |
| egg phosphatide | 1.2 |
| glycerol | 2.25 |
| disodium edetate dihydrate | 0.0055 |
| sodium hydroxide | q.s. |
| water for injection | to 100 |
| (ii) Injection 2 | |
| 'Active Compound' | 1.0 |
| soybean oil | 5.0 |
| fractionated coconut oil | 5.0 |
| egg phosphatide | 1.2 |
| glycerol | 2.25 |
| disodium edetate dihydrate | 0.0055 |
| sodium hydroxide | q.s. |
| water for injection | to 100 |
| (iii) Injection 3 | |
| 'Active Compound' | 1.0% w/v |
| N-methylpyrrolidinone | 30% w/v |
| propylene glycol | 40% w/v |
| water for injection | to 100 |
| (iv) Injection 4 | |
| 'Active Compound' | 2.0% w/v |
| N-methylpyrrolidinone | 30% w/v |
| propylene glycol | 40% w/v |
| water for injection | to 100 |
| (v) Injection 5 | |
| 'Active Compound' | 1.0 |
| soybean oil | 1.0–3.0 |
| lecithin | 1.2 |
| glycerol | 2.25 |
| sodium hydroxide | q.s. |
| water for injection | to 100 |
| (vi) Injection 6 | |
| 'Active Compound' | 1.0% w/v |
| soybean oil | 10.0% w/v |
| safflower oil | 10.0% w/v |
| egg phosphatids | 1.2% w/v |
| glycerol | 2.5% w/v |
| sodium hydroxide | q.s. |
| water | to 100 |
| (vii) Injection 7 | |
| 'Active Compound' | 1.0% w/v |
| soybean oil | 10.0% w/v |
| egg phosphatids | 1.2% w/v |
| glycerol | 2.5% w/v |
| sodium hydroxide | q.s. |
| water for injection | to 100 |
| (viii) Injection 8 | |
| 'Active Compound' | 1.0% w/v |
| soybean oil | 30.0% w/v |
| phosphatidylcholine from egg yolk | 1.2% w/v |
| glycerol | 1.67% w/v |
| sodium hydroxide | q.s. |
| water for injection | to 100 |
| (ix) Injection 9 | |
| 'Active Compound' | 10.0% w/v |
| caprylic/capric triglyceride | 10.0% w/v |
| egg phosphatides | 1.2% w/v |
| glycerol | 2.5% w/v |
| sodium hydroxide | q.s. |
| water | to 100 |
| (x) Injection 10 | |
| 'Active Compound' | 5.0% w/v |
| caprylic/capric triglyceride | 15.0% w/v |
| egg phosphatides | 1.2% w/v |
| glycerol | 2.5% w/v |
| sodium hydroxide | q.s. |
| water | to 100 |
| (xi) Injection 11 | |
| 'Active Compound' | 10% w/v |
| Miglyol ® 810 | 5.0–10.0% w/v |
| egg yolk phosphatides | 0.5–1.0% w/v |
| DMPG | 0.1% w/v |
| glycerol | 2.25% w/v |
| sodium hydroxide | q.s. |
| water | to 100 |
| (xii) Injection 12 | |
| 'Active Compound' | 5% w/v |
| Miglyol ® 810 | 20% w/v |
| egg yolk phosphatides | 0.5–1.0% w/v |
| glycerol | 2.25% w/v |
| sodium hydroxide | q.s. |
| water | to 100 |

-continued

| | wt % |
|---|---|
| (xiii) Injection 13 | |
| 'Active Compound' | 4.0–10.0% w/v |
| vegetable oil | 0.5–20.0% w/v |
| egg yolk phosphatides | 0.5–1.2% w/v |
| glycerol | 0.5–2.5% w/v |
| sodium hydroxide | q.s. |
| water | to 100 |

The above formulations can be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A pharmaceutical composition comprising a pharmaceutically acceptable carrier and a compound selected from the group consisting of:

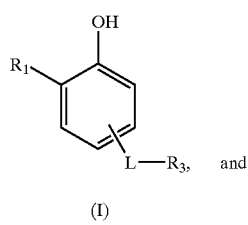

formula (I)

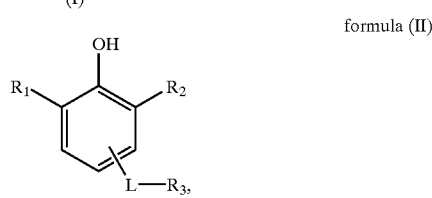

formula (II)

wherein
$R_1$ and $R_2$ are each independently $(C_1-C_8)$alkyl, $(C_3-C_8)$cycloalkyl, or $(C_3-C_8)$cycloalkyl$(C_1-C_8)$alkyl;
L is selected from the group consisting of a covalent bond, $(C_1-C_6)$alkylene, $(C_2-C_6)$alkenylene, and $(C_2-C_6)$alkynylene; provided that when the compound is a compound of formula (I), L is not a covalent bond; and
$R_3$ is selected from the group consisting of —C(=O)OR$_a$, —C(=O)SR$_a$, —P(=O)(OR$_a$)$_2$, —C(=O)OCH$_2$C(=O)N(R$_a$)$_2$, and —C(=O)OC(=O)R$_a$ wherein each R$_a$ is independently selected from a hydrocarbyl group containing from 1 to 20 carbon atoms and optionally containing from 1 to 5 heteroatoms selected from the group consisting of halo, nitrogen, oxygen and sulfur;
or a pharmaceutically acceptable salt thereof.

2. The composition of claim 1, wherein
$R_3$ is selected from the group consisting of —C(=O)OR$_a$, —C(=O)SR$_a$, —P(=O)(OR$_a$)$_2$, —C(=O)OCH$_2$C(=O)N(R$_a$)$_2$, and —C(=O)OC(=O) R$_a$ wherein R$_a$ is selected from the group consisting of $(C_1-C_8)$alkyl, $(C_2-C_8)$alkenyl, $(C_2-C_8)$alkynyl, $(C_3-C_8)$cycloalkyl, $(C_3-C_8)$cycloalkenyl, $(C_3-C_8)$cycloalkyl$(C_1-C_8)$alkyl, $(C_3-C_8)$cycloalkenyl$(C_1-C_8)$alkyl, aryl, aryl$(C_1-C_8)$alkyl, aryl$(C_1-C_8)$alkenyl, and aryl$(C_1-C_8)$alkynyl, wherein any $(C-C_8)$alkyl, $(C_1-C_8)$alkenyl, $(C_1-C_8)$alkynyl $(C_3-C_8)$cycloalkyl, or aryl is optionally substituted by one or more substituents independently selected from the group consisting of halo, cyano, $(C_1-C_8)$alkoxycarbonyl, $(C_1-C_8)$alkanoyl, and $(C_1-C_8)$alkoxy.

3. The composition of claim 2, wherein $R_3$ is —C(=O)OR$_a$, —C(=O)SR$_a$, or —C(=O)OC(=O)R$_a$ wherein R$_a$ is selected from the group consisting of $(C_1-C_8)$alkyl, $(C_2-C_8)$alkenyl, $(C_2-C_8)$alkynyl, $(C_3-C_8)$cycloalkyl, aryl, aryl$(C_1-C_8)$alkyl, aryl$(C_1-C_8)$alkenyl, or aryl$(C_1-C_8)$alkynyl.

4. The composition of claim 3, wherein $R_1$ and $R_2$, are each independently selected from the group consisting of $(C_1-C_8)$alkyl and $(C_3-C_8)$cycloalkyl.

5. The composition of claim 4, wherein L is selected from the group consisting of methylene, ethylene, vinylene, propylene, allylene, butylene, pentylene, or hexylene.

6. The composition of claim 5, wherein $R_1$ and $R_2$ are each independently isopropyl, 2-butyl, 2-pentyl, 3-pentyl, 2-hexyl, 3-hexyl, cyclopropyl, cyclobutyl, cyclopentyl or cyclohexyl.

7. The composition of claim 6, wherein $R_3$ is —C(=O)OR$_a$ wherein R$_a$ is selected from the group consisting of$(C_1-C_8)$alkyl, $(C_2-C_8)$alkenyl, $(C_2-C_8)$alkynyl, $(C_3-C_8)$cycloalkyl, aryl, aryl$(C_1-C_8)$alkyl, aryl$(C_1-C_8)$alkenyl, or aryl$(C_1-C_8)$alkynyl.

8. The composition of claim 2, wherein the compound comprises formula (I).

9. The composition of claim 8, wherein $R_1$ is $(C_1-C_8)$ alkyl and $(C_3-C_6)$cycloalkyl.

10. The composition of claim 2, wherein the compound comprises formula (II).

11. The composition of claim 10, wherein $R_1$ and $R_2$ are each independently $(C_1-C_6)$alkyl and $(C_3-C_6)$cycloalkyl.

12. The composition of claim 2, wherein the compound comprises a compound of formula (III):

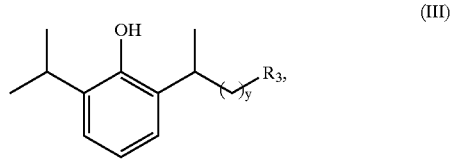

wherein y is 0, 1, 2, 3, 4, 5, or 6.

13. The composition of claim 12, wherein $R_3$ is —C(=O)OR$_a$ and R$_a$ is selected from the group consisting of$(C_1-C_8)$ alkyl, $(C_2-C_8)$alkenyl, and $(C_2-C_8)$alkynyl.

14. The composition of claim 10, wherein the compound comprises a compound of formula (IV):

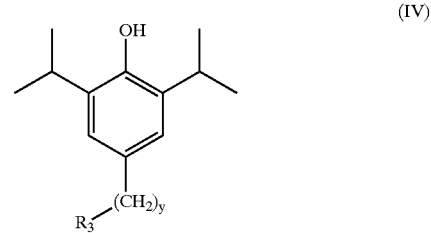

wherein y is 0, 1, 2, 3, 4, 5, or 6.

15. The composition of claim 2, wherein the compound comprises a compound of formula (X):

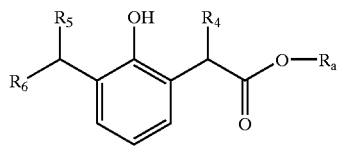

wherein
- R₄ is $(C_1-C_5)$alkyl, $(C_2-C_5)$alkenyl, or $(C_2-C_5)$ alkynyl;
- R₅ is $(C_1-C_6)$cycloalkyl$(C_1-C_6)$alkyl; and
- R₆ is methyl;
- or R₅ and R₆ together with the carbon atom to which they are attached form a $(C_{3-8})$cycloalkyl; and
- R_a is $(C_1-C_8)$alkyl, $(C_2-C_8)$alkenyl, $(C_2-C_8)$alkynyl or $(C_3-C_8)$cycloalkyl.

16. The composition of claim 15, wherein R₄ is methyl or ethyl; R₅ is independently methyl or ethyl; or R₅ and R₆ together with the carbon atom to which they are attached form a $(C_{3-6})$cycloalkyl; and R_a is ethyl, propyl, isopropyl or 2-butyl.

17. The composition of claim 1, wherein the composition further comprises another therapeutic agent selected from the group consisting of an anesthetic, a sedative, and an analgesic.

18. A method for inducing or maintaining anesthesia or sedation in a mammal, comprising administering to the mammal an effective amount of a composition of claim 1.

19. A method for inducing or maintaining anesthesia or sedation in a mammal, comprising administering to the mammal an effective amount of a composition of claim 2.

20. A method for inducing or maintaining anesthesia or sedation in a mammal, comprising administering to the mammal an effective amount of a compostion of claim 15.

21. A compound of formula (V):

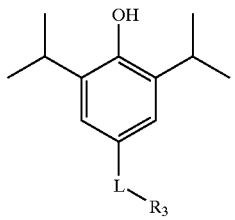

wherein L is a covalent bond, methylene, or ethylene; and

R₃ is selected from the group consisting of —C(=))OR_a, —C(=O)SR_a, —C(=O)OCH₂C(=O)N(R_a)₂, and —C(=O)OC(=O)R_a wherein each R_a is independently selected from a hydrocarbyl group containing from 1 to 20 carbon atoms and optionally containing from 1 to 5 heteroatoms selected from the group consisting of halo, nitrogen, oxygen and sulfur;

provided when L is a covalent bond, R₃ is not —C(=O)OR_a wherein R_a is methyl, ethyl, 1,2-dibromoethyl, but-2-enyl, hexadecyl, stearyl, or benzyl; and provided when L is ethylene, R₃ is not —C(=O)OR_a wherein R_a is methyl or stearyl;

or a pharmaceutically acceptable salt thereof.

22. A compound of formula (X):

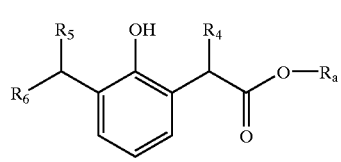

wherein

- R₄ is $(C_1-C_5)$alkyl, $(C_2-C_5)$alkenyl, or $(C_2-C_5)$alkynyl;
- R₅ is $(C_1-C_6)$alkyl, $(C_3-C_8)$cycloalkyl, or $(C_3-C_8)$cycloalkyl$(C_1-C_6)$alkyl; and R₆ is methyl;
- or R₅ and R₆ together with the carbon atom to which they are attached form a $(C_{3-8})$cycloalkyl; and
- (R₆ is $(C_1-C_8)$alkyl, $(C_2-C_8)$alkenyl, $(C_2-C_8)$alkynyl or $(C_3-C_8)$cycloalkyl.

23. The compound of claim 22, wherein R₄ is methyl or ethyl; R₅ is methyl or ethyl; or R₅ and R₆ together with the carbon atom to which they are attached form a $(C_{3-6})$cycloalkyl; and R_a is ethyl, propyl, or isopropyl.

* * * * *

UNITED STATES PATENT AND TRADEMARK OFFICE
CERTIFICATE OF CORRECTION

PATENT NO.   : 6,815,555 B2
DATED        : November 9, 2004
INVENTOR(S)  : Jenkins et al.

It is certified that error appears in the above-identified patent and that said Letters Patent is hereby corrected as shown below:

Column 25,
Line 52, replace "$OR_3$" with -- $OR_a$, --.

Column 27,
Line 12, replace "$R_5$ is $(C_1-C_6)$cycloalkyl$(C_1-C_6)$alkyl;" with
-- $R_5$ is $(C_1-C_6)$alkyl, $(C_3-C_8)$cycloalkyl, or $(C_3-C_8)$cycloalkyl$(C_1-C_6)$alkyl; --.

Signed and Sealed this

Twenty-sixth Day of April, 2005

JON W. DUDAS
*Director of the United States Patent and Trademark Office*